(12) United States Patent
Becker

(10) Patent No.: US 12,193,801 B2
(45) Date of Patent: Jan. 14, 2025

(54) IMPLANTABLE SYSTEM FOR DETECTING ELECTRICAL SIGNALS OF A HUMAN HEART OR AN ANIMAL HEART

(71) Applicant: BIOTRONIK SE & Co. KG, Berlin (DE)

(72) Inventor: Frank Becker, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 714 days.

(21) Appl. No.: 16/997,114

(22) Filed: Aug. 19, 2020

(65) Prior Publication Data

US 2021/0068671 A1 Mar. 11, 2021

(30) Foreign Application Priority Data

Sep. 6, 2019 (EP) .................................... 19195857

(51) Int. Cl.
*A61B 5/0245* (2006.01)
*A61B 5/00* (2006.01)

(52) U.S. Cl.
CPC .......... *A61B 5/0245* (2013.01); *A61B 5/0004* (2013.01); *A61B 5/6869* (2013.01); *A61B 5/72* (2013.01)

(58) Field of Classification Search
CPC ... A61B 5/0245; A61B 5/0004; A61B 5/6869; A61B 5/72
See application file for complete search history.

(56) References Cited

U.S. PATENT DOCUMENTS

| 8,509,896 | B2 | 8/2013 | Doerr et al. |
| 2005/0137632 | A1 | 6/2005 | Ding et al. |
| 2009/0112276 | A1 | 4/2009 | Yu et al. |
| 2010/0262204 | A1 | 10/2010 | McCabe et al. |
| 2011/0029035 | A1* | 2/2011 | Vollkron ............ A61N 1/36843 607/25 |
| 2018/0110980 | A1 | 4/2018 | Taff |
| 2019/0046802 | A1 | 2/2019 | Min et al. |

FOREIGN PATENT DOCUMENTS

EP 2060299 A1 5/2009

* cited by examiner

*Primary Examiner* — Joseph M Dietrich
(74) *Attorney, Agent, or Firm* — Laurence A. Greenberg; Werner H. Stemer; Ralph E. Locher

(57) ABSTRACT

An implantable system detecting electrical signals of a human or animal heart includes a processor, a memory unit, a first detection unit for atrial activity, a second detection unit for right ventricular activity and a third detection unit for left ventricular activity. The system automatically performs steps at regular intervals including detecting an intrinsic right atrial activity using the first detection unit; detecting an intrinsic right ventricular activity using the second detection unit; determining a time between the intrinsic right atrial activity and the intrinsic right ventricular activity, and storing this time as atrioventricular conduction time. Additionally or alternatively the steps include detecting an intrinsic right ventricular activity using the second detection unit; detecting an intrinsic left ventricular activity using the third detection unit; and determining a time between the intrinsic right ventricular activity and the intrinsic left ventricular activity, and storing this time as interventricular conduction time.

15 Claims, 1 Drawing Sheet

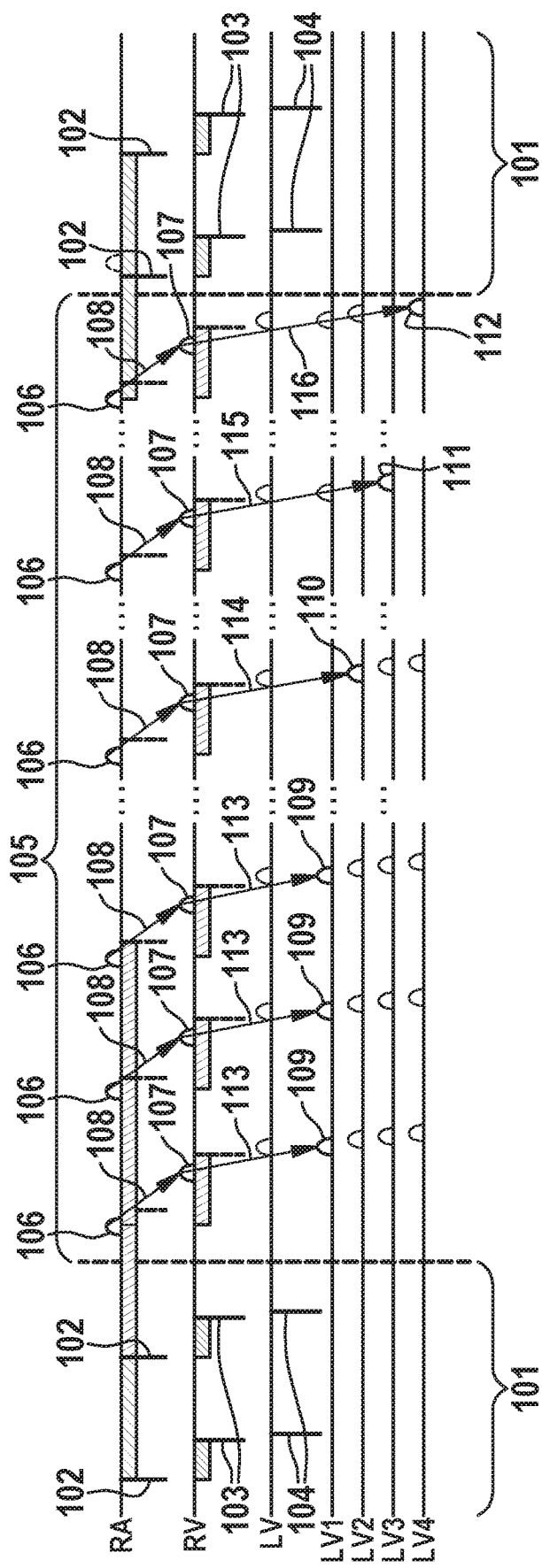

IMPLANTABLE SYSTEM FOR DETECTING ELECTRICAL SIGNALS OF A HUMAN HEART OR AN ANIMAL HEART

CROSS-REFERENCE TO RELATED APPLICATION

This application claims the priority, under 35 U.S.C. § 119, of European Patent Application EP 19195857, filed Sep. 6, 2019; the prior application is herewith incorporated by reference in its entirety.

BACKGROUND OF THE INVENTION

Field of the Invention

The present invention relates to an implantable system for detecting electrical signals of a human heart or an animal heart, including a processor, a memory unit, a first detection unit for detecting an atrial activity, a second detection unit for detecting a right ventricular activity, and a third detection unit for detecting a left ventricular activity. The invention also relates to a method for controlling the operation of an implantable system for detecting electrical signals of a human heart or an animal heart and to a computer program product including computer-readable code, which prompts a processor to carry out steps when the code is being executed on the processor.

The atrioventricular conduction time and the interventricular conduction time are two important characteristic variables from which the condition of a human heart or an animal heart can be inferred, and which must be taken into consideration during the operation of a cardiac pacemaker, so that the pulses emitted by the cardiac pacemaker result in effective stimulation of the treated heart.

The atrioventricular conduction time is the time that passes between a stimulation or an intrinsic activity of the atrium and an immediately following ventricular activity. The interventricular conduction time indicates the temporal offset between a contraction of the right ventricle and the contraction of the left ventricle following immediately thereafter. In a healthy heart, the right ventricle and the left ventricle contract at the same time. In patients suffering from cardiological diseases, however, a temporal offset may occur. As a result, the heart's ability to pump properly declines, which is manifested in cardiac insufficiency and an enlarged heart. In order to achieve a contraction of both ventricles in a better synchronized manner in terms of time in such a case, it is necessary to determine the temporal offset between the contraction of the left ventricle and the contraction of the right ventricle with great precision. This typically takes place after the implantation of a pacemaker. The problem in this regard is that the interventricular conduction time can change, in particular during the initial time following the implantation of the pacemaker, but in principle also at a later time. It is then necessary to readjust the pacemaker so as to achieve good therapeutic effectiveness of the pacemaker. In the case of left ventricular leads having multiple stimulation poles, such as quadrupolar leads, a measurement of the interventricular conduction time between the right ventricle and each of the left ventricular stimulation poles can be carried out. The optimal stimulation pole is selected based on the measured times.

U.S. Patent Application Publication No. 2010/0100148 A1 describes the option of determining the atrioventricular conduction time and the interventricular conduction time within the scope of a stimulation threshold test of a cardiac pacemaker. The problem with that determination method is that an extrinsic stimulation of the heart in question is carried out, which may overlap the intrinsic cardiac activity.

BRIEF SUMMARY OF THE INVENTION

It is accordingly an object of the present invention to provide an implantable medical device and a method for controlling the operation of the device, which overcome the hereinafore-mentioned disadvantages of the heretofore-known devices and methods of this general type and which also allow a simplified and reliable determination of the atrioventricular conduction time and/or of the interventricular conduction time after the medical device has been implanted.

With the foregoing and other objects in view there is provided, in accordance with the invention, an implantable system for detecting electrical signals of a human heart or an animal heart, comprising a processor, a memory unit, a first detection unit, a second detection unit, and a third detection unit. The first detection unit is used to detect an atrial activity, that is, an activity in an atrium of the human or animal heart, and in particular in the right atrium. The second detection unit is used to detect a right ventricular activity, while the third detection unit is used to detect a left ventricular activity of a human heart or an animal heart.

According to the invention, the system is characterized in that the memory unit includes a computer-readable program, which prompts the processor to automatically carry out the steps described hereinafter at regular intervals when the program is being executed on the processor.

According to a first variant, initially an intrinsic right atrial activity is detected by way of the first detection unit. Thereafter, an intrinsic right ventricular activity immediately following the previously detected right atrial activity is detected by way of the second detection unit. Afterwards, the time that has passed between the intrinsic right atrial activity and the intrinsic right ventricular activity is determined. This is subsequently stored as the atrioventricular conduction time, for example in the memory unit.

As an alternative or in addition to the steps described above, the program can prompt the processor to carry out the steps described hereinafter.

According to this second variant, initially an intrinsic right ventricular activity is detected by way of the second detection unit. Thereafter, an intrinsic left ventricular activity immediately following the previously detected intrinsic right ventricular activity is detected by way of the third detection unit. Afterwards, the time that has passed between the intrinsic right ventricular activity and the intrinsic left ventricular activity is determined. This is then stored as the interventricular conduction time, for example in the memory unit.

In contrast to the medical devices known from the prior art, the implantable system claimed in the present invention is aimed at exclusively detecting an intrinsic activity (action) of the individual chambers of a human heart or an animal heart. External stimuli, which are emitted, for example, by a stimulation unit of a cardiac pacemaker, are expressly not evaluated. Moreover, the implantable system claimed in the present invention is configured to automatically carry out the described method steps at regular intervals. In this way, it is possible at all times to provide reliable data regarding the atrioventricular conduction time and/or the interventricular conduction time. This data can then be used to set the parameters of a cardiac pacemaker or of another device for stimulating a human heart or an animal heart. It can also be used as starting data for subsequent diagnostic examinations. For example, a change in the condition of the heart can be ascertained from monitoring the chronological progression of the atrioventricular conduction time or the interventricular conduction time. A physician can then decide on suitable counter-measures with respect to the observed change in the condition of the heart. Moreover, based on such data, a physician is also able to assess whether a device for stimulating the heart is functioning correctly and behaving as desired with respect to the cardiological condition of the patient.

In one variant, it is not just the right ventricular activity and the left ventricular activity that are detected within the scope of the determination of the interventricular conduction time. Rather, an intrinsic right atrial activity is also detected in this variant by way of the first detection unit. It is then possible to provide particularly reliable information that the detected ventricular activities were in fact triggered by an intrinsic atrial signal of the particular heart.

When the intrinsic right atrial activity is detected by way of the first detection device, the atrioventricular conduction time can additionally be determined in a further variant, so that both the atrioventricular conduction time and the interventricular conduction time are determined within one measuring cycle. This variant is consequently a combination of the two variants described above.

In one variant, the program prompts the processor to carry out the above-described steps for the determination of the atrioventricular conduction time and/or the interventricular conduction time once within a time period of 3 hours to 48 hours, in particular of 6 hours to 36 hours, and in particular of 12 hours to 24 hours. For example, the program can prompt the processor to carry out the described steps once a day. It is then possible to ascertain and store the atrioventricular conduction time and/or the interventricular conduction time particularly easily at a defined interval.

In one variant, the implantable system is not only suitable for detecting electrical signals of a human heart or an animal heart, but also provided and configured to stimulate the same human or animal heart. The determined atrioventricular conduction time and/or the determined interventricular conduction time can then be used particularly easily for adapting parameters (for example, the AV delay or the VV delay) of the same device, which also carries out a stimulation of the heart if necessary.

In one variant, the implantable system is a cardiac pacemaker, and in particular a device for cardiac resynchronization therapy (CRT device). The reason is that it is particularly relevant in the case of such cardiac pacemakers or CRT devices to precisely set the stimulation pulses to be delivered when needed to the physiological circumstances in the particular heart. As a result of the ascertainment of the atrioventricular conduction time and/or of the interventricular conduction time, a particularly meaningful parameter setting can thus be implemented at the cardiac pacemaker or CRT device.

In one variant, the program prompts the processor to inhibit an atrial stimulation and a ventricular stimulation until the atrioventricular conduction time and/or the interventricular conduction time have been determined. In this way, it is ensured that no extrinsic stimulation signals can be detected, which can, in principle, be delivered by the implantable system, configured in this variant as a stimulation unit, to the human or animal heart in question, and which can overlap the intrinsic signals of the cardiac activity. Since it only takes very little time to carry out the above-described steps for determining the atrioventricular conduction time and/or the interventricular conduction time, inhibiting stimulation pulses during the required measuring time is not problematic for the safety of the device and/or the state of health of the patient.

In one variant, the program prompts the processor to carry out the above-described steps for the determination of the atrioventricular conduction time and/or the interventricular conduction time during a routine measurement of a signal of the intrinsic cardiac activity. As an alternative or in combination, the above-described steps can be carried out during a determination and/or an adaptation of a detection threshold of the implantable system.

The routine measurement of a signal of the intrinsic cardiac activity and the determination and/or adaptation of a detection threshold of the implantable system are typically carried out once a day. During this time, the delivery of stimulation pulses is generally suppressed anyway. The method for ascertaining the atrioventricular conduction time and/or the interventricular conduction time carried out by the system claimed in the present invention can, in this variant, be carried out without any significant loss of time during the routine measurement of a signal of the intrinsic cardiac activity, or during the determination and/or adaptation of a detection threshold of the implantable system. In this way, it is additionally possible, when the implantable system is already being tested anyway with respect to the response behavior thereof, to ascertain the atrioventricular conduction time and/or the interventricular conduction time, except without significant additional time expenditure. As a result, this variant in particular offers a particularly simple option for implementing the automatic regular ascertainment of the atrioventricular conduction time and/or of the interventricular conduction time.

According to one embodiment of the device according to the invention, the measurement of a signal of the intrinsic cardiac activity encompasses the measurement and/or determination of at least one signal parameter of amplitude, pulse width, number of zero crossings, amplitude and/or phase frequency spectrum and/or energy of the signal, as well as the parameters

- of a model of the signal (such as autoregressive moving average (ARMA)) and/or
- of a transformation of the signal (such as wavelet) and/or amplitude, pulse width, number of zero crossings, amplitude and/or phase frequency spectrum and/or energy of a time derivative of the signal.

In one variant, the program prompts the processor to store a plurality (two or more) of previously determined atrioventricular conduction times and/or interventricular conduction times. The storing can take place in the memory unit of the implantable system, for example. Such storing of the previously determined conduction times allows a history of the conduction times already ascertained to be compiled. It is then possible, for example, to ascertain to what extent a newly determined conduction time differs from conduction times ascertained in the past. The two conduction time types (that is, the atrioventricular conduction times on the one hand, and the interventricular conduction times on the other hand) are typically stored separately from one another in the process and compared to one or more conduction times of the same time as needed.

In one variant, the program prompts the processor to ascertain a chronological progression of the particular conduction time from the plurality of stored atrioventricular conduction times and/or interventricular conduction times. For this purpose, the individual conduction times are stored together with a piece of time information with respect to the point in time of the determination thereof. It is then possible to ascertain a chronological progression of the corresponding conduction time particularly easily. A trend of one of the two conduction times, or of both conduction times, in a particular direction can be ascertained from this chronological progression, which allows a change in the condition of the heart in question to be inferred. As an alternative or in addition, the data obtained in this way can also be used to infer the interaction between the implantable system and the heart, of which the signals are detected.

In one variant, the program prompts the processor to transmit the atrioventricular conduction time and/or the interventricular conduction time to an external device or to an external data center. In this way, the obtained data can be evaluated particularly easily outside the implantable system. The data transmission to an external device can be useful, in particular, within the scope of individual examinations of a patient by a physician. In contrast, a data transmission to a data center allows continuous monitoring of the condition of the implantable system that is sending the data, or of the patient in whom the system was implanted. In this way, results that allow improved patient care and/or enhanced device safety can be obtained within the scope of telemedicine. The data transmission to an external device or to a data center takes place, in particular, wirelessly in a radio-based way. For this purpose, the implantable system is, in this variant, equipped with a corresponding radio module.

In one variant, the implantable system includes a multipolar electrode. The first detection unit represents a first electrode pole of the multipolar electrode, while the second detection unit represents a second electrode pole of the multipolar electrode. The multipolar electrode can include 2, 3, 4, 5, or 6 electrode poles, for example, wherein a larger number of electrode poles is, in principle, likewise conceivable. In this way, the implantable system can be configured with a floating electrode, for example, which detects both atrial cardiac signals and ventricular cardiac signals by way of the different electrode poles thereof.

In one variant, it is contemplated that the multipolar electrode not only includes the first detection unit and the second detection unit, but additionally also the third detection unit.

In a further variant, the third detection unit itself is configured as a multipolar electrode. This means, in this variant, that it has a plurality (two or more) of electrode poles. Each of these electrode poles is used to detect an intrinsic left ventricular signal. In this variant, it is thus possible to ascertain different left ventricular signals and thus, with respect to a respective right ventricular signal detected immediately before, (slightly) different interventricular conduction times. In one variant, it is possible to calculate a uniform interventricular conduction time from the previously ascertained individual interventricular conduction times, for example by finding a mean value. It is also conceivable to allocate a higher weight to isolated previously determined individual interventricular conduction times than others of the previously determined individual conduction times if this appears physiologically useful based on the configuration of the individual electrode poles inside the heart of a patient.

The third detection unit can, for example, be configured as a quadrupolar electrode, that is, to include four electrode poles, which each detect a left ventricular signal. The cardiac signals that are indicative of a left ventricular activity are typically detected by an electrode that is anchored at the coronary sinus of a heart, since a direct insertion of the electrode into the left ventricle is generally not possible due to the pressure conditions present there.

With the objects of the invention in view, there is also provided a method for controlling the operation of an implantable system for detecting electrical signals of a human heart or an animal heart. This control method refers, in particular, to the control of the operation of an implantable system according to the above descriptions. The method comprises the steps described hereinafter.

Initially, in a first variant, an intrinsic right atrial activity is detected by way of a first detection device. Afterwards, an intrinsic right ventricular activity, which immediately follows the previously detected right atrial activity, is detected by way of a second detection unit. Thereafter, the time that has passed between the intrinsic right atrial activity and the intrinsic right ventricular activity is ascertained. This time is then stored as the atrioventricular conduction time.

As an alternative or in addition to the above-described first variant, the second variant of the method described hereinafter can be carried out. According to this variant, initially an intrinsic right ventricular activity is detected by way of a second detection unit. Furthermore, an intrinsic left ventricular activity immediately following the previously detected right ventricular activity is detected by way of a third detection unit. Afterwards, the time that has passed between the intrinsic right ventricular activity and the intrinsic left ventricular activity is determined. This time is then stored as the interventricular conduction time.

With the objects of the invention in view, there is furthermore provided a computer program product including computer-readable code, which prompts a processor to carry out the method steps described hereinafter when the code is being executed on the processor.

Initially, in a first variant, an intrinsic right atrial activity is detected by way of a first detection device. Afterwards, an intrinsic right ventricular activity, which immediately follows the previously detected right atrial activity, is detected by way of a second detection unit. Thereafter, the time that has passed between the intrinsic right atrial activity and the intrinsic right ventricular activity is ascertained. This time is then stored as the atrioventricular delay.

As an alternative or in addition to the above-described first variant, the second variant of the method described hereafter can be carried out. According to this variant, initially an intrinsic right ventricular activity is detected by way of a second detection unit. Furthermore, an intrinsic left ventricular activity immediately following the previously detected right ventricular activity is detected by way of a third detection unit. Afterwards, the time that has passed between the intrinsic right ventricular activity and the intrinsic left ventricular activity is determined. This time is then stored as the interventricular conduction time.

With the objects of the invention in view, there is concomitantly provided a method for treating a human patient or an animal patient in need of such treatment. This method is carried out by way of an implantable system for detecting electrical signals of the patient's heart, and in particular an implantable system according to the above description. The implantable system comprises a processor, a memory unit, and three detection units. A first detection unit is used to detect an atrial activity. A second detection unit is used to detect a right ventricular activity. A third detection unit is used to detect a left ventricular activity. The method comprises the steps described hereafter.

According to a first variant, an intrinsic right atrial activity is detected by way of the first detection device. Thereafter, an intrinsic right ventricular activity immediately following the previously detected intrinsic right atrial activity is detected by way of the second detection unit. Thereafter, the time that has passed between the intrinsic right atrial activity and the intrinsic right ventricular activity is determined. This time is then stored as the atrioventricular conduction time.

As an alternative or in addition to the above-described first variant, it is also possible for the second variant of the method described hereinafter to be carried out. According to the second variant, initially an intrinsic right ventricular activity is detected by way of the second detection unit. Thereafter, an intrinsic left ventricular activity immediately following the previously detected right ventricular activity is detected by way of the third detection unit. Finally, the time that has passed between the intrinsic right ventricular activity and the intrinsic left ventricular activity is determined. This time is then stored as the interventricular conduction time.

Regardless of whether the first and/or second variants of the method are carried out, the determined conduction times (that is, the atrioventricular conduction time and/or the interventricular conduction time) are used thereafter to adapt the chronological sequence of stimulation pulses that are delivered by a system suitable for delivering such stimulation pulses. This delivery can be used to stimulate the heart of the patient as a substitute for absent intrinsic cardiac pulses or activities, or else to support a weak or insufficient intrinsic cardiac function. The system that is suitable for delivering stimulation pulses can be the same system that is also used for detecting the cardiac signals. This means that a device, such as a cardiac pacemaker or a CRT device, can be used both for the detection of cardiac signals or a cardiac activity, and for the stimulation of the same heart.

All variants and alternative embodiments described in connection with the implantable system can be arbitrarily combined with one another and applied to the described methods and the described computer program product. The described variants of the methods can further be arbitrarily combined with one another and applied to the respective other methods and to the computer program product and the system. Similarly, the described variants of the computer program product can be arbitrarily combined with one another and applied to the described methods and the described system.

Other features which are considered as characteristic for the invention are set forth in the appended claims.

Although the invention is illustrated and described herein as embodied in an implantable system for detecting electrical signals of a human heart or an animal heart and a method for controlling the operation of the system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE SEVERAL VIEWS OF THE DRAWING

The FIGURE of the drawing is a schematic flow chart showing a method for determining the atrioventricular conduction time and the interventricular conduction time by way of a cardiac pacemaker.

DETAILED DESCRIPTION OF THE INVENTION

Referring now in detail to the single FIGURE of the drawing, there is seen a schematic flow chart of a program for determining the atrioventricular conduction time and the interventricular conduction time by way of a cardiac pacemaker. The individual lines indicate the chambers of the heart in which a signal can be detected or delivered by way of the cardiac pacemaker. RA denotes the right atrium, RV denotes the right ventricle, and LV denotes the left ventricle. Since the cardiac pacemaker in the illustrated exemplary embodiment includes a quadrupolar left ventricular electrode, the left ventricular signals can be distinguished as a first left ventricular signal LV1, a second left ventricular signal LV2, a third left ventricular signal LV3, and a fourth left ventricular signal LV4.

In a first operating program 101 carried out by default, first stimulation pulses 102 can be delivered to the right atrium, second stimulation pulses 103 can be delivered to the right ventricle, and third stimulation pulses 104 can be delivered to the left ventricle.

In a measuring program 105, the actual or possible delivery of such stimulation pulses 102, 103, 104 is completely inhibited, which is illustrated by the dotted vertical lines in the temporal area of the measuring program 105. During the measuring program 105, consequently only an intrinsic activity of the heart of the patient wearing the cardiac pacemaker can be ascertained.

A right atrial signal detection 106 is carried out at regular intervals for detecting such an intrinsic cardiac activity. Likewise, a right ventricular signal detection 107 is carried out at regular intervals. A temporal offset between the detected right atrial signals 106 and the immediately following detected right ventricular signals 107 reflects the atrioventricular conduction time 108.

First left ventricular signals 109, second left ventricular signals 110, third left ventricular signals 111, and fourth left ventricular 112 can be detected by way of the different left ventricular channels. A detection of only one type of left ventricular signals is permitted at a given point in time. A detection of the other left ventricular signals, in contrast, is inhibited. As a result, either only first left ventricular signals 109 or second left ventricular signals 110 or third left ventricular signals 111 or fourth left ventricular 112 can be detected at a point in time.

A first temporal offset between the detected right ventricular signals 107 and the detected immediately following first left ventricular signals 109 represents a first interventricular conduction time 113.

A second temporal offset between the detected right ventricular signals 107 and the detected immediately following second left ventricular signals 110 represents a second interventricular conduction time 114.

A third temporal offset between the detected right ventricular signals 107 and the immediately following third left ventricular signals 111 represents a third interventricular conduction time 115.

Finally, a fourth temporal offset between the detected right ventricular signals 107 and the immediately following fourth left ventricular signals 112 represents a fourth interventricular conduction time 116.

The first interventricular conduction time 113, the second interventricular conduction time 114, the third interventricular conduction time 115, and the fourth interventricular conduction time 116 can be the same or different from one another, depending on how the individual electrodes that are used for detecting the different left ventricular signals are disposed within the heart, and depending on how the physiological stimuli conduction occurs in the heart in question.

The measuring program 105 can be carried out in such a way that an interventricular conduction time is ascertained based on different detected cardiac signal groups (optionally immediately following one another), as is shown by way of example for the first interventricular conduction time 113. In this way, the first interventricular conduction time 113 is ascertained based on three signal groups, which are each composed of a right ventricular signal 107 and a first left ventricular signal 109.

Likewise, it is possible to evaluate only individual cardiac signals so as to ascertain a conduction time, as is shown by way of example for the second interventricular conduction time 114, the third interventricular conduction time 115, and the fourth interventricular conduction time 116.

In the illustrated exemplary embodiment, the measuring program 105 is carried out when the corresponding cardiac pacemaker routinely carries out the measurement of a signal of the intrinsic cardiac activity and the determination and/or adaptation of a detection threshold of the implantable system. Such an ascertainment typically takes place once a day. The atrioventricular conduction time 108 and the different interventricular conduction times 113, 114, 115, 116 are consequently also ascertained once a day. When the conduction times have been ascertained, and the routine measurement of a signal of the intrinsic cardiac activity and the determination and/or adaptation of a detection threshold of the implantable system have been carried out, the cardiac pacemaker returns to the standard operating program 101, in which right atrial stimulation pulses 102 as well as right ventricular stimulation pulses 103 and left ventricular stimulation pulses 104 can be delivered. An inhibition of these stimulation pulses is thus only necessary during the measuring program 105 and provided to detect in fact, at this point in time, only the intrinsic cardiac signals that reflect the intrinsic cardiac activity in the different compartments of the heart.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An implantable system for detecting electrical signals of a human heart or an animal heart, the implantable system comprising:
   a processor, a memory unit, a first detection unit for detecting an atrial activity, a second detection unit for detecting a right ventricular activity, and a third detection unit for detecting a left ventricular activity,
   said memory unit including a computer-readable program prompting said processor to automatically carry out steps at regular intervals upon said program being executed on said processor, said steps including at least one of:
   a1) detecting an intrinsic right atrial activity by using said first detection unit;
   b1) detecting an intrinsic right ventricular activity by using said second detection unit; and
   c1) determining a time having passed between the intrinsic right atrial activity and the intrinsic right ventricular activity, and storing said time as an atrioventricular conduction time;
   or
   a2) detecting an intrinsic right ventricular activity by using said second detection unit;
   b2) detecting an intrinsic left ventricular activity by using said third detection unit; and
   c2) determining a time having passed between the intrinsic right ventricular activity and the intrinsic left ventricular activity, and storing said time as an interventricular conduction time; and
   said program being configured to prompt said processor to carry out said steps during at least one of a determination or an adaptation of a detection threshold of the implantable system when a delivery of stimulation pulses is suppressed.

2. The implantable system according to claim 1, wherein step a1), in addition to steps a2) and b2), is carried out prior to step c2).

3. The implantable system according to claim 1, wherein said program prompts said processor to carry out said steps once within a time period of from 3 hours to 48 hours.

4. The implantable system according to claim 1, wherein the implantable system is provided and configured to stimulate the human heart or animal heart having the activity to be detected by the implantable system.

5. The implantable system according to claim 1, wherein said program prompts said processor to inhibit an atrial stimulation and a ventricular stimulation until a determination of at least one of said atrioventricular conduction time or said interventricular conduction time.

6. The implantable system according to claim 1, wherein said program prompts said processor to carry out said steps at least one of:
   during a routine measurement of a signal of the intrinsic cardiac activity of the implantable system, or
   during at least one of a determination or an adaptation of a detection threshold of the implantable system.

7. The implantable system according to claim 6, wherein said measurement of the signal of the intrinsic cardiac activity encompasses a measurement of at least one signal parameter of amplitude, pulse width, number of zero crossings, at least one of amplitude or phase frequency spectrum or energy of the signal, as well as parameters of at least one of:
   a model of the signal, or
   a transformation of the signal, or
   an amplitude, pulse width, number of zero crossings, at least one of amplitude or phase frequency spectrum or energy of a time derivative of the signal.

8. The implantable system according to claim 1, wherein said program prompts said processor to store a plurality of at least one of previously determined atrioventricular conduction times or interventricular conduction times.

9. The implantable system according to claim 8, wherein said program prompts said processor to ascertain a chronological progression of a particular conduction time from said plurality of at least one of stored atrioventricular conduction times or interventricular conduction times.

10. The implantable system according to claim 1, wherein said program prompts said processor to transmit at least one of an atrioventricular conduction time or an interventricular conduction time to an external device or to a data center.

11. The implantable system according to claim 1, which further comprises a multipolar electrode, said first detection unit being a first electrode pole of said multipolar electrode, and said second detection unit being a second electrode pole of said multipolar electrode.

12. The implantable system according to claim 1, wherein said third detection unit includes a plurality of electrode poles each provided for detecting an intrinsic left ventricular activity.

13. A method for controlling an operation of an implantable system for detecting electrical signals of a human heart or an animal heart, the method comprising at least one of steps:
   a1) detecting an intrinsic right atrial activity by using a first detection unit;
   b1) detecting an intrinsic right ventricular activity by using a second detection unit; and
   c1) determining a time having passed between the intrinsic right atrial activity and the intrinsic right ventricular activity, and storing the time as an atrioventricular conduction time;
   or steps:
   a2) detecting an intrinsic right ventricular activity by using the second detection unit;
   b2) detecting an intrinsic left ventricular activity by using a third detection unit; and
   c2) determining a time having passed between the intrinsic right ventricular activity and the intrinsic left ventricular activity, and storing the time as an interventricular conduction time; and
   carrying out the steps during at least one of a determination or an adaptation of a detection threshold of the implantable system when a delivery of stimulation pulses is suppressed.

14. A non-transitory computer program product including computer-readable code prompting a processor to carry out steps as follows upon the code being executed on the processor, the steps including at least one of:
   a1) detecting an intrinsic right atrial activity by using a first detection unit;
   b1) detecting an intrinsic right ventricular activity by using a second detection unit; and
   c1) determining a time having passed between the intrinsic right atrial activity and the intrinsic right ventricular activity, and storing the time as an atrioventricular conduction time;
   or
   a2) detecting an intrinsic right ventricular activity by using the second detection unit;
   b2) detecting an intrinsic left ventricular activity by using a third detection unit; and
   c2) determining a time having passed between the intrinsic right ventricular activity and the intrinsic left ventricular activity, and storing the time as an interventricular conduction time; and
   carrying out the steps during at least one of a determination or an adaptation of a detection threshold of an implantable system when a delivery of stimulation pulses is suppressed.

15. A method for treating a human patient or an animal patient requiring a treatment by using an implantable system for detecting electrical signals of the heart of the patient, the method comprising:
   providing the implantable system with a processor, a memory unit, a first detection unit for detecting an atrial activity, a second detection unit for detecting a right ventricular activity, and a third detection unit for detecting a left ventricular activity;
   carrying out steps including at least one of:
   a1) detecting an intrinsic right atrial activity by using the first detection unit;
   b1) detecting an intrinsic right ventricular activity by using the second detection unit; and
   c1) determining a time having passed between the intrinsic right atrial activity and the intrinsic right ventricular activity, and storing the time as an atrioventricular conduction time;
   or
   a2) detecting an intrinsic right ventricular activity by using the second detection unit;
   b2) detecting an intrinsic left ventricular activity by using the third detection unit; and
   c2) determining a time having passed between the intrinsic right ventricular activity and the intrinsic left ventricular activity, and storing the time as an interventricular conduction time;
   carrying out steps a1) to c2) during at least one of a determination or an adaptation of a detection threshold of the implantable system when a delivery of stimulation pulses is suppressed; and
   d) using at least one of the determined atrioventricular conduction time or the determined interventricular conduction time for adapting a chronological sequence of stimulation pulses delivered by a system for stimulating the heart of the patient as a substitute for intrinsic cardiac pulses or for supporting an intrinsic cardiac function.

* * * * *